(12) United States Patent
Schrott

(10) Patent No.: US 8,491,875 B2
(45) Date of Patent: Jul. 23, 2013

(54) HAIR VOLUMIZING COMPOSITIONS

(75) Inventor: Adam Patrick Schrott, Cincinnati, OH (US)

(73) Assignee: Kao Corporation, Tokyo (JP)

( * ) Notice: Subject to any disclaimer, the term of this patent is extended or adjusted under 35 U.S.C. 154(b) by 15 days.

(21) Appl. No.: 13/207,035

(22) Filed: Aug. 10, 2011

(65) Prior Publication Data
US 2012/0045409 A1  Feb. 23, 2012

Related U.S. Application Data

(60) Provisional application No. 61/374,892, filed on Aug. 18, 2010.

(51) Int. Cl.
*A61K 8/92* (2006.01)
*A61K 8/89* (2006.01)
*A61Q 5/02* (2006.01)
*A61Q 5/06* (2006.01)

(52) U.S. Cl.
USPC .................. 424/70.11; 424/70.22; 424/70.15; 424/70.21

(58) Field of Classification Search
None
See application file for complete search history.

(56) References Cited

U.S. PATENT DOCUMENTS

| 4,963,348 | A | | 10/1990 | Bolich, Jr. et al. |
| 5,306,488 | A | * | 4/1994 | Vanlerberghe et al. ...... 424/70.8 |
| 6,696,050 | B2 | | 2/2004 | Barbuzzi et al. |
| 6,706,258 | B1 | | 3/2004 | Gallagher et al. |
| 6,787,130 | B2 | | 9/2004 | Dhamdhere et al. |
| 7,598,213 | B2 | | 10/2009 | Geary et al. |
| 2003/0091521 | A1 | | 5/2003 | Midha et al. |
| 2004/0115151 | A1 | | 6/2004 | Giroud |
| 2006/0029562 | A1 | | 2/2006 | Lane et al. |
| 2009/0074697 | A1 | * | 3/2009 | Huynh ....................... 424/70.13 |

FOREIGN PATENT DOCUMENTS

WO    WO 01/39735    6/2001

OTHER PUBLICATIONS

"Hair Care Products: What are the benefits of Bees Wax in Your Hair?" http://www.essortment.com/hair-care-products-benefits-bees-wax-hair-60633.html, printed Sep. 15, 2011.
"Hair Wax," Wikipedia, http://en.wikipedia.org/wiki/Hair_wax, printed Sep. 15, 2011.

* cited by examiner

*Primary Examiner* — Robert A Wax
*Assistant Examiner* — Sarah Park
(74) *Attorney, Agent, or Firm* — Frost Brown Todd LLC

(57) ABSTRACT

Volumizing compositions, including shampoos, which provide volume, body, fullness, movement and/or stylability benefits to the hair are disclosed. The compositions contain a waxy material selected from natural waxes of animal or plant origin, alkyl-modified dimethicones, copolymers of vinyl pyrrolidone and long chain alpha-olefins, synthetic wax/highly branched polyalpha olefin polymers and mixtures thereof. The compositions are substantially free of materials which form an oily coating on the hair, such as dimethicone gums, oils, triglycerides, petrolatums, unsaturated fatty acids, oils, $C_{18}$-$C_{28}$ mono-long chain alkyl quaternary ammonium materials, and combinations of those materials. Shampoo compositions and the method of providing volume to the hair, utilizing the defined waxy materials, are also disclosed.

7 Claims, No Drawings

HAIR VOLUMIZING COMPOSITIONS

BACKGROUND

This application is related to and claims priority from U.S. Provisional Patent Application No. 61/374,892, filed Aug. 18, 2010, incorporated herein by reference.

The look of fullness of hair is a positive, desirable and sought-after characteristic for many people. That is one of the reasons why clean hair looks good. When hair is dirty, oil and sebum on the hair make it appear to be flat; it lacks fullness, feels weighted down, is stiff and difficult to style. On the other hand, clean hair has a fullness and bounciness which makes it look good. It is also easier to style. Fullness is particularly desirable and difficult to obtain with some of the current hair care products which tend to deposit oily conditioning materials on the hair, which can make it appear to be flat and lack volume.

Achieving this fullness characteristic in hair is called volumizing. A composition which provides a fullness and bounciness to hair, even hair that is not completely clean, is called a volumizing composition and provides a very desirable benefit. The present invention defines hair compositions (such as shampoos, conditioners and volumizing sprays) that provide improved volume, body, fullness, movement and/or stylability to hair. This is achieved using a specific class of waxy materials which is defined herein. While some of these waxy materials are known for use in hair conditioning compositions, in combination with conditioning materials such as silicones and long chain quaternary ammonium compounds, for the purpose of providing conditioning benefits, they have not heretofore been used on their own to provide volumizing benefits.

Waxy materials, such as beeswax and candelilla wax, have been used at high levels in hair waxes and hair pomades to provide shape and styling to hair.

U.S. Pat. No. 6,787,130, Dhandhere et al, issued Sep. 7, 2004, describes the use of silicone pressure sensitive adhesives (PSA's) in shampoos and conditioners to provide a hair volumizing benefit. The silicone PSA includes a polydimethylsiloxane gum component and a silicone resin component. The defined compositions and examples include standard conditioning materials, such as mono-long chain quaternary ammonium materials, silicone liquid, and long chain alcohols, which are minimized in the present invention.

U.S. Published Patent Application 2008/0112904, Chan et al, published May 15, 2008, teaches the use of particles of cationic guar gum cross-linked with glyoxal in shampoos and conditioners to provide hair volumizing benefits.

PCT Published Patent Application WO 01/39735, Venkateswaran et al, published Jun. 7, 2001, discloses conditioning shampoos comprising an anionic surfactant, a cationic silicone emulsion which includes a cationic surfactant and a mechanically-emulsifiable silicone compound (which can be a silicone resin) having a defined particle size, and an aqueous carrier. The disclosed compositions include standard conditioning materials, such as mono-long chair quaternary ammonium materials, silicone liquid, and long chain alcohols, which are minimized in the present invention.

SUMMARY

The present invention provides a volumizing composition which comprises a carrier and from about 0.1% to about 2% of a waxy material having a melting point of from about 55° C. to about 75° C. selected from natural waxes of animal or plant origin, alkyl-modified dimethicones, copolymers of vinyl pyrrolidone and long chain alpha-olefins, synthetic wax/highly branched polyalpha-olefin polymers, and mixtures thereof, wherein said volumizing composition is substantially free from hair treatment materials which form an oily coating on the hair.

One specific embodiment of the invention encompasses a volumizing shampoo which comprises from about 0.5% to about 20% of a surfactant, water, and from about 0.1% to about 2% of a waxy material having a melting point of from about 55° C. to about 75° C. selected from natural waxes of animal or plant origin, alkyl-modified dimethicones, copolymers of vinyl pyrrolidone and long chain alpha-olefins, synthetic wax/highly branched polyalpha-olefin polymers, and mixtures thereof, wherein the shampoo is substantially free of materials which form an oily coating on the hair.

The present invention additionally encompasses a method of providing volume to hair by depositing on the hair a volumizing amount of a waxy material having a melting point of from about 55° C. to about 75° C. selected from natural waxes of animal or plant origin, alkyl-modified dimethicones, copolymers of vinyl pyrrolidone and long chain alpha-olefins, synthetic wax/highly branched polyalpha-olefin polymers, and mixtures thereof, from a composition which is substantially free of hair treatment materials which form an oily coating on the hair.

As used herein, all percentages and ratios are "by weight" unless otherwise specified.

Further, all patents, patent applications and publications referenced in this application are incorporated herein by reference.

DETAILED DESCRIPTION

This application relates to hair care compositions which provide improved volume, body, fullness, movement and/or stylability to hair. The compositions may be in any form and include, for example, shampoos, conditioners, styling compositions (liquid or spray) or volumizing compositions (liquid or spray).

The compositions of the present invention are substantially free of materials that can form an oily coating on hair. Such materials include dimethicone gums, oils, triglycerides, petrolatums, unsaturated $C_{20}$ and greater fatty alcohols, and $C_{18}$-$C_{28}$ mono-long chain quaternary ammonium materials, as well as mixtures of those materials. By "substantially free" is meant that the compositions of the present invention include no more than about 3%, for example, no more than about 2%, no more than about 1%, and no more than about 0.5% of the materials described above, in total. In practice, it is believed that the "good" materials (of the present invention) leave a light, slightly stiff, naturally smooth feeling film on the hair which helps to hold the hair up while also facilitating the ability to form a good "volume" style. In contrast, the "bad" materials, defined above, maintain their liquid or paste nature on the hair forming an oily or greasy feeling film that weighs down the hair and provides no significant hold or stylability to the hair.

The compositions of the present invention include from about 0.1% to about 2%, for example from about 0.1% to about 1%, of a waxy material having a melting point between about 55° C. and 75° C. These materials are selected from the following: natural waxes of animal or plant origin, alkyl-modified dimethicones, copolymers of vinyl pyrrolidone and long chain alpha-olefins, synthetic wax/highly branched polyalpha-olefin polymers, and mixtures of those materials. Specific examples of such materials which can be used in the present invention include $C_{24}$-$C_{26}$ alkyl dimethicone, candelilla wax, bees wax, tricontanyl polyvinyl pyrrolidone (PVP), and mixtures thereof. It is these materials which provide the volumizing and styling benefits seen with the present invention. As used herein, the term "melting point" has the following meaning: where dealing with a specific compound having a narrow molecular weight range, the term has its standard definition (i.e., the temperature at which the solid melts and turns to liquid)—under those circumstances, the melting point is usually sharply defined. On the other hand, where the material has a distribution of molecular weights (as is frequently the case here), the transition is less sharply defined and the melting point is defined as the temperature at which the material begins to soften or melt.

If the composition of the present invention is a shampoo, it additionally contains from about 0.5% to about 20% of a surfactant material. Surfactants utilized in shampoo compositions are well-known in the art and are disclosed, for example, in U.S. Pat. No. 6,706,258, Gallagher et al, issued Mar. 16, 2004, and U.S. Pat. No. 7,598,213, Geary et al, issued Oct. 6, 2009, both of which are incorporated herein by reference.

Shampoo compositions of the present invention comprise one or more cleansing surfactants which are cosmetically acceptable and suitable for topical application to the hair. Suitable cleansing surfactants, which may be used singularly or in combination, are selected from anionic, nonionic, amphoteric and zwitterionic surfactants, and mixtures thereof.

Examples of anionic surfactants include alkyl sulfates, alkyl ether sulfates, alkaryl sulfonates, alkanoyl isethionates, alkyl succinates, alkyl sulfosuccinates, N-alkyl sarcosinates, alkyl phosphates, alkyl ether phosphates, alkyl ether carboxylates, and alpha olefin sulfonates, especially their sodium, magnesium, ammonium and mono-, di- and triethanolamine salts. The alkyl and acyl groups generally contain from 8 to 18 carbon atoms and may be saturated or unsaturated. The alkyl ether sulfates, alkyl ether phosphates and alkyl ether carboxylates may contain from 1 to 10 ethylene oxide or propylene oxide units per molecule. Typical anionic surfactants for use in shampoos of the present invention include sodium oleyl succinate, ammonium lauryl sulfosuccinate, ammonium lauryl sulfate, sodium dodecylbenzene sulfonate, triethanolamine dodecylbenzene sulfonate, sodium cocoylisethionate, sodium lauryl isethionate and sodium N-lauryl sarcosinate. Particularly preferred anionic surfactants include sodium lauryl sulfate, triethanolamine monolauryl phosphate, sodium lauryl ether sulfate (1EO, 2EO and 3EO), ammonium lauryl sulfate and ammonium lauryl ether sulfate (1EO, 2EO and 3EO).

Examples of amphoteric and zwitterionic surfactants include alkyl amine oxides, alkyl betaines, alkyl amidopropyl betaines, alkyl sulfobetaines (sultaines), alkyl glycinates, alkylcarboxy glycinates, alkyl amphopropionates, alkyl amphoglycinates, alkyl amidopropyl hydroxysultaines, acyl taurates and acyl glutamates, wherein the alkyl and acyl groups have from 8 to 19 carbon atoms (and may be saturated or unsaturated). Typical amphoteric and zwitterionic surfactants for use in shampoos of the present invention include lauryl amine oxide, cocodimethyl sulfopropyl betaine, lauryl betaine, cocamidopropyl betaine and sodium cocamphopropionate.

Representative nonionic surfactants that can be included in the shampoo compositions of the present invention include the condensation products of aliphatic ($C_8$-$C_{18}$) primary or secondary linear or branched chain alcohols or phenols with alkylene oxides, usually ethylene oxide, and generally having from 6 to 30 ethylene oxide groups. Other representative nonionic surfactants include mono- or di-alkyl alkanolamides. Examples include coco mono- or di-ethanolamide and coco monoisopropylamide.

Additional nonionic surfactants which can be included in shampoo compositions of the present invention are the alkyl polyglycosides (APGs). Typically the APG is one which comprises an alkyl group connected (optionally via a bridging group) to a block of one or more glycosyl groups. Suitable alkyl polyglycosides for use in the present invention are commercially available and include, for example, those materials identified as Oramix NS10 from Seppic, Plantaren 1200 and Plantaren 2000 from Henkel.

The balance of the composition comprises a carrier which is a liquid compatible with both the included hair care ingredients and is suitable for topical application to the hair. The carrier is typically water, ethanol or mixtures of those materials and is most preferably water, particularly for shampoo compositions. It should be removable from the hair (e.g., by drying or volatilization) and should not leave an oily coating on the hair.

The compositions of the present invention may contain additional conventional hair care ingredients used at their conventional levels. Examples of such materials include viscosity control agents, colorants, pH adjusting agents, preservatives, fragrances, antimicrobials, opacifying agents, pearlescing agents, sunscreens, chelating agents (for example, EDTA), antioxidants, and polyols (for example glycerine or polypropylene glycol), or combinations of those materials. The materials are used at their art-disclosed levels to achieve their known effects. Specific examples of materials which can be used in the present compositions include up to about 2% of a hair compatible acid (preferably from about 0.2 to about 0.6%), such a lactic acid, malic acid, tartaric acid, fumaric acid and/or isononanoic acid. The compositions may also include up to about 8% (preferably from about 4% to about 6%) of a $C_{14}$-$C_{18}$ fatty alcohol, such as cetyl alcohol, ceteareth alcohol, stearyl alcohol, steareth alcohol, and mixtures of those materials. The compositions can also include up to about 5% (preferably from about 0.2% to about 0.4%) of an ester material (such as isopropyl palmitate or isodecyl neopentanoate) and/or linear or branched hydrocarbons (such as isohexadecane or hydrogenated polyisobutene). Finally, the compositions can include up to about 3% (preferably from about 1% to about 2%) of an alkyl amine or ammonium material selected from alkyl amidoamines, alkyl amidopropyl dimethylamines, and alkyl oxypropyl trimonium chloride.

The present invention also encompasses a method of providing volume to hair by depositing on the hair a volumizing amount of the waxy materials defined herein from a composition which is substantially free of hair treatment materials which form an oily coating on the hair. The waxy material is typically deposited onto the hair from one of the compositions defined in the present application. The waxy material is deposited in a "volumizing amount" by which is meant an amount sufficient to provide the volumizing benefits of the present invention, but not so high as to leave an unwanted residue on the hair. This amount can be determined for a given waxy material in a given formulation using conventional techniques.

The compositions may be applied to the hair from shampoos or other types of hair care compositions, such as serums, liquids, mousses, aerosols, pump sprays. The carrier vehicles for each type of these compositions is well-known in the art.

The compositions of the present invention are made using conventional techniques known in the art. The general description of one such procedure follows. In the main vessel, add purified water and heat to 80° C. Add components (A)

which include water-soluble ingredients (such as pH regulators, salts, glycerin). Mix until homogeneous. Components (B) comprise the "oil phase" and should be pre-mixed in a separate vessel, heated to 80° C., and mixed until homogeneous. The oil phase components are added to the main vessel with mixing to form an emulsion. The resulting emulsion is cooled to 40° C., and the remaining components (C) may be added with sufficient mixing to incorporate them into the emulsion.

EXAMPLES 1-6

Six compositions of the present invention, in the form of volumizing conditioner compositions, are made by mixing the ingredients defined in the table below together, using the procedure described above. When these compositions are applied to the hair, they provide the user with the volumizing and styling benefits described in this application.

|   | Conditioner Formulations | 1 | 2 | 3 | 4 | 5 | 6 |
|---|---|---|---|---|---|---|---|
| A | pH Regulator (Lactic Acid, Malic Acid, Tartaric Acid, Fumaric Acid, Isononanoic Acid) | qs | qs | qs | qs | qs | qs |
|   | Glycerin |  | 1.00 |  |  | 1.00 |  |
| B | Cetearyl Alcohol | 5.00 | 5.00 | 5.00 | 5.00 | 6.00 | 6.00 |
|   | Isopropyl Palmitate | 0.20 | 0.20 | 0.20 | 0.20 |  |  |
|   | Cetyl Esters |  |  |  |  | 0.50 | 0.50 |
|   | Behenamidopropyl Dimethylamine | 1.50 | 1.50 | 1.50 | 1.50 |  |  |
|   | Cetrimonium Chloride (30% Active) |  |  |  |  | 5.00 | 5.00 |
|   | C24-26 Alkyl Dimethicone | 0.30 |  |  | 0.15 | 0.30 | 0.15 |
|   | Tricontanyl PVP |  | 0.20 |  |  |  |  |
|   | Candelilla Wax |  |  |  | 0.15 |  | 0.15 |
|   | Bees Wax |  |  | 0.20 |  |  |  |
| C | Preservative | qs. | qs | qs | qs | qs | qs |
|   | Fragrance | qs | qs | qs | qs | qs | qs |
|   | Water | Balance | Balance | Balance | Balance | Balance | Balance |
|   | Target pH |  |  | 3.5-5.0 |  |  |  |

EXAMPLES 7-9

Shampoo compositions of the present invention, having the components listed below, are made using the procedure described above. When these compositions are applied to hair, as with conventional shampoos, they clean and provide volumizing benefits to the hair, as described in this application.

|   | Shampoo Formulation | 7 | 8 | 9 |
|---|---|---|---|---|
| A | Sodium Laureth Sulfate (70%) | 14.000 | 14.000 | 14.000 |
|   | Sodium Lauryl Sulfate (30%) | 13.500 | 13.500 | 13.500 |
|   | Cocamidopropyl Betaine (30%) | 6.500 | 6.500 | 6.500 |
|   | Cocamide MEA | 0.750 | 0.750 | 0.750 |
|   | Disodium EDTA | 0.050 | 0.050 | 0.050 |
|   | Polyquaternium-10 | 0.200 |  | 0.200 |
|   | Catonic Guar Gum |  | 0.050 |  |
| B | Cocamide MEA | 0.600 | 0.750 | 0.750 |
|   | EGDS | 0.300 | 0.300 | 0.300 |
|   | Cetyl Alcohol | 0.200 | 0.200 | 0.200 |
|   | Benzyl Alcohol | 0.500 | 0.500 | 0.500 |
|   | C24-26 Alkyl Dimethicone | 0.20 |  | 0.10 |
|   | Tricontanyl PVP |  | 0.20 | 0.10 |
| C | Fragrance | qs | qs | qs |
|   | Preservative | qs | qs | qs |
|   | Viscosity Adjuster (Sodium Chloride) | qs | qs | qs |
|   | pH Regulator (Lactic Acid, Malic Acid, Tartaric Acid, Fumaric Acid) |  | To pH 5.0-6.0 |  |
|   | Water | Balance | Balance | Balance |

What is claimed is:

1. A volumizing shampoo which comprises from about 0.5% to about 20% of a surfactant selected from anionic surfactants, amphoteric surfactants, zwitterionic surfactants, and mixtures thereof, from about 0.1% to about 2% of a waxy material having a melting point of from about 55° C. to about 75° C. selected from natural waxes of animal or plant origin, alkyl-modified dimethicones, copolymers of vinyl pyrrolidone and long chain alpha-olefins, synthetic wax/highly branched polyalpha-olefin polymers, and mixtures thereof, and the balance of the composition water; wherein said shampoo contains no greater than about 2% of hair treatment materials which form an oily coating on the hair selected from the group consisting of dimethicone gums, oils, triglycerides, petrolatums, unsaturated fatty acids, $C_{18}$-$C_{28}$ mono-long chain quaternary ammonium materials, and mixtures thereof.

2. The shampoo according to claim 1 which comprises from about 0.1 to about 1% of the waxy material.

3. The shampoo according to claim 2 wherein the waxy material is selected from $C_{24}$-$C_{26}$ alkyl dimethicone, candelilla wax, bees wax, tricontanyl PVP, and mixtures thereof.

4. A volumizing composition which comprises
a carrier;
from about 0.1% to about 1% of a waxy material having a melting point of from about 55° C. to about 75° C. selected from natural waxes of animal or plant origin, alkyl-modified dimethicones, copolymers of vinyl pyrrolidone and long chain alpha-olefins, synthetic wax/highly branched polyalpha-olefin polymers, and mixtures thereof;
from about 0.2% to about 0.6% of lactic acid;
from about 4% to about 6% of cetearyl alcohol and/or stearyl alcohol;
from about 0.2% to about 0.4% of isopropyl myristate and/or isopropyl palmitate;
from about 1% to about 2% of behenamidopropyl dimethylamine; and
the balance water;

wherein said volumizing composition contains no greater than about 2% of hair treatment materials which form an oily coating on the hair selected from dimethicone gums, oils, triglycerides, petrolatums, unsaturated fatty acids, $C_{18}$-$C_{28}$ mono-long chain alkyl quaternary materials, and mixtures thereof.

5. The volumizing composition according to claim 4 wherein the waxy material is selected from $C_{24}$-$C_{26}$ alkyl dimethicone, candelilla wax, bees wax, tricontanyl PVP, and mixtures thereof.

6. The volumizing composition according to claim 4 wherein the carrier is selected from water, ethanol, and mixtures thereof.

7. A method for providing volume to hair by depositing on the hair a composition according to claim 4.

* * * * *